United States Patent
Plos

(10) Patent No.: US 6,840,964 B1
(45) Date of Patent: Jan. 11, 2005

(54) OXIDATION DYEING METHOD USING N-ACETYCLYSTEINE AS A REDUCING AGENT AND LACCASE AS AN OXIDATING AGENT

(75) Inventor: Grégory Plos, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/926,209

(22) PCT Filed: Feb. 24, 2000

(86) PCT No.: PCT/FR00/00456

§ 371 (c)(1),
(2), (4) Date: Sep. 25, 2001

(87) PCT Pub. No.: WO00/57848

PCT Pub. Date: Oct. 5, 2000

(30) Foreign Application Priority Data

Mar. 26, 1999 (FR) ............................................. 99 03829

(51) Int. Cl.$^7$ ................................................. A61K 7/13
(52) U.S. Cl. ..................... 8/405; 8/406; 8/408; 8/410; 8/421; 8/429; 8/435; 8/554; 8/581; 8/606
(58) Field of Search ........................... 8/401, 405, 406, 8/408, 410, 412, 421, 429, 435, 554, 581, 606

(56) References Cited

U.S. PATENT DOCUMENTS

| | | | | |
|---|---|---|---|---|
| 3,251,742 A | | 5/1966 | Solway .......................... | 167/88 |
| 5,104,413 A | * | 4/1992 | Ikeda ............................. | 8/405 |
| 5,735,908 A | * | 4/1998 | Cotteret et al. ................. | 8/405 |
| 6,106,579 A | * | 8/2000 | Kunz et al. .................... | 8/432 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| EP | 0 429 855 | 6/1991 |
| EP | 0 504 005 | 9/1992 |
| EP | 0 673 641 | 9/1995 |
| EP | 0 716 846 | 6/1996 |
| EP | 1142561 | 10/2001 |
| EP | 1142562 | 10/2001 |
| FR | 2 112 549 | 6/1973 |
| FR | 2 586 913 | 3/1987 |
| FR | 2 694 018 | 1/1994 |
| GB | 1026978 | 4/1966 |
| GB | 1153196 | 5/1969 |
| WO | 94/08969 | 4/1994 |
| WO | 94/08970 | 4/1994 |
| WO | 95/07998 | 3/1995 |
| WO | 95/33836 | 12/1995 |
| WO | 95/33837 | 12/1995 |
| WO | 96/00290 | 1/1996 |
| WO | 97/19998 | 6/1997 |
| WO | 97/19999 | 6/1997 |
| WO | WO 97/19999 | * 6/1997 ............ A61K/7/13 |

* cited by examiner

*Primary Examiner*—Brian P. Mruk
*Assistant Examiner*—Eisa Elhilo
(74) *Attorney, Agent, or Firm*—Jacobson Holman PLLC

(57) ABSTRACT

The present invention relates to a method for dyeing keratin fibers especially human keratin fibers such as hair, characterized in that it consists in the following: a dyeing composition (A) is applied to the fibers, whereby said dyeing composition contains at least one oxidation dye precursor in an appropriate medium and optionally one or several couplers in addition to N-acetylcysteine as a reducing agent; the color is revealed in the presence of air in an alkaline, neutral or acidic medium with the aid of laccase, whereby said laccase is incorporated into composition (A) or composition (B); compositions (A) and (B) are immediately mixed before used or applied successively to keratin fibers.

33 Claims, No Drawings

OXIDATION DYEING METHOD USING N-ACETYCLYSTEINE AS A REDUCING AGENT AND LACCASE AS AN OXIDATING AGENT

This is a nationalization of PCT/FR00/00456 filed Feb. 24, 2000 and published in French.

The present invention relates to a process for the oxidation dyeing of keratin fibres, and in particular of human keratin fibres such as the hair, using compositions comprising, in a medium which is suitable for dyeing, at least one oxidation dye precursor, optionally, one or more couplers, and N-acetylcysteine as reducing agent, and at least one laccase as oxidizing agent.

It is known practice to dye keratin fibres, and in particular the hair, with dye compositions containing oxidation dye precursors, which are generally known as "oxidation bases" in particular ortho- or para-phenylenediamines, ortho- or para-aminophenols and heterocyclic bases.

Oxidation dye precursors are initially colourless or only faintly coloured compounds which develop their dyeing power on the hair in the presence of an oxidizing agent. The oxidizing agent used is generally hydrogen peroxide. The formation of coloured compounds results either from a self-condensation of the "oxidation bases" or from a condensation of the "oxidation bases" with coloration modifier compounds, or "couplers", which are generally present in the dye compositions used in oxidation dyeing and which are represented more particularly by meta-phenylenediamines, meta-aminophenols and meta-diphenols and certain heterocyclic compounds.

The variety of molecules used which consist, on the one hand, of the "oxidation bases" and, on the other hand, of the "couplers", allows a wide range of colours to be obtained.

The oxidation dyeing of keratin fibres may also be achieved using oxidizing systems other than hydrogen peroxide, such as enzymatic systems. Thus, it has already been proposed in U.S. Pat. No. 3,251,742 and patent applications FR-A-2 112 549, FR-A-2 694 018, EP-A-0 504 005, WO 95/07998, WO 95/33836, WO 95/33837, WO 96/00290, WO 97/19998 and WO 97/19999 to dye keratin fibres with compositions comprising at least one oxidation dye in combination with enzymes of the laccase type, said compositions being placed in contact with atmospheric oxygen. Specifically, it has been observed that aqueous hydrogen peroxide solution can cause degradation of hair fibres and also a partial attack of the melanin of the hair, resulting in lightening of the fibre.

In order to be able to conserve the oxidation dye precursors and couplers, it is necessary to combine them with a reducing agent.

However, the Applicant has found that these reducing agents generally impede the rise of the dyes on the fibres, which is reflected by less luminous shades and less intense colorations.

In order to obtain an equivalent chromaticity, it is thus necessary to use larger amounts of dyes.

Furthermore, many reducing agents used hitherto have an inhibitory action on laccase activity.

After considerable research conducted in this matter, the Applicant has just discovered that using N-acetylcysteine as reducing agent when a laccase is used as oxidizing agent makes it possible to solve the problems mentioned above.

Specifically, it has been found that N-acetylcysteine does not inhibit laccase activity; furthermore, it has been found, surprisingly, that the mixture thus produced does not impede the rise of the oxidation dyes on the hair.

These compositions moreover give rise to more chromatic (more luminous) shades and to more intense colorations when compared with equivalent compositions containing usual reducing agents and oxidizing agents.

The colorations obtained moreover show good resistance to perspiration, light and shampooing.

The invention also makes it possible to reduce the amount of colorant active materials used in the dye compositions when compared with the conventional techniques known in the prior art.

One subject of the present invention is thus the use of N-acetylcysteine as reducing agent and of a laccase as oxidizing agent for oxidation dyeing.

Another subject of the invention relates to a process for dyeing keratin fibres, and in particular human keratin fibres such as the hair, which consists:

in applying to the fibres a dye composition (A) containing, in a medium which is suitable for dyeing, at least one oxidation dye precursor and, optionally, one or more couplers and, as reducing agent, N-acetylcysteine, and in developing the colour in the presence of air in alkaline, neutral or acidic medium using a laccase as oxidizing agent, the laccase being incorporated into the composition (A), in this case stored protected from air, or into a composition (B), the compositions (A) and (B) being, in this second case, mixed immediately before use or applied one after the other to the keratin fibres.

In one preferred embodiment of the invention, the N-acetylcysteine is present in proportions of from 0.005% to 2% relative to the total weight of the composition (A) and even more preferably from 0.01% to 0.25%.

The laccase(s) used in the process in accordance with the invention may be chosen in particular from laccases of plant origin, of animal origin, of fungal origin (yeasts, moulds, fungi) or of bacterial origin, the organisms of origin possibly being monocellular or multicellular. They can be obtained by biotechnology.

Among the laccases of plant origin which may be used according to the invention, mention may be made of the laccases produced by plants which carry out chlorophyll synthesis, such as those mentioned in patent application FR-A-2 694 018, for instance those found in extracts of *Anacardiacea* plants such as, for example, extracts of *Magnifera indica, Schinus molle* or *Pleiogynium timoriense;* in extracts of *Podocarpacea* plants; of *Rosmarinus* off.; of *Solanum tuberosum;* of *Iris* sp.; of *Coffea* sp.; of *Daucus carrota;* of *Vinca minor;* of *Persea americana;* of *Catharanthus roseus;* of *Musa* sp.; of *Malus pumila;* of *Gingko biloba;* of *Monotropa hypopithys* (Indian pipe); of *Aesculus* sp:; of *Acer pseudoplatanus;* of *Prunus persica* and of *Pistacia palaestina.*

Among the laccases of fungal origin, optionally obtained by biotechnology, which can be used according to the invention, mention may be made of the laccase(s) obtained from *Polyporus versicolor,* from *Rhizoctonia praticola* and from *Rhus vernicifera* as described, for example, in patent applications FR-A-2 112 549 and EP-A-504 005; the laccases described in patent applications WO 95/07988, WO 95/33836, WO 95/33837, WO 96/00290, WO 97/19998 and WO 97/19999, the content of which forms an integral part of the present description, such as, for example, the laccase (s) obtained from *Scytalidium,* from *Polyporus pinsitus,* from *Myceliophthora thermophila,* from *Rhizoctonia solani,* from *Pyricularia orizae,* and variants thereof. Mention may also be made of the laccase(s) obtained from *Trametes versicolor,* from *Fomes fomentarius,* from *Chaetomium thermophile,* from *Neurospora crassa,* from *Coriolus versicol,* from *Botrytis cinerea,* from *Rigidoporus lignosus,* from *Phellinus noxius,* from *Pleurotus ostreatus,* from

*Aspergillus nidulans,* from *Podospora anserina,* from *Agaricus bisporus,* from *Ganoderma lucidum,* from *Glomerella cingulata,* from *Lactarius piperatus,* from *Russula delica,* from *Heterobasidion annosum,* from *Thelephora terrestris,* from *Cladosporium cladosporioides,* from *Cerrena unicolor,* from *Coriolus hirsutus,* from *Ceriporiopsis subvermispora,* from *Coprinus cinereus,* from *Panaeolus papilionaceus,* from *Panaeolus sphinctrinus,* from *Schizophyllum commune,* from *Dichomitius squalens,* and from variants thereof.

Laccases of fungal origin, optionally obtained by biotechnology, will more preferably be chosen.

The enzymatic activity of the laccases of the invention having syringaldazine among their substrates can be defined by the oxidation of syringaldazine under aerobic conditions. One Lacu unit corresponds to the amount of enzyme which catalyses the conversion of 1 mmol of syringaldazine per minute at pH 5.5 and at 30° C. One u unit corresponds to the amount of enzyme which produces an absorbance delta of 0.001 per minute at a wavelength of 530 nm, using syringaldazine as substrate, at 30° C. and at pH 6.5.

The enzymatic activity of the laccases of the invention can also be defined by the oxidation of para-phenylenediamine. One ulac unit corresponds to the amount of enzyme which produces an absorbance delta of 0.001 per minute at a wavelength of 496.5 nm, using para-phenylenediamine as substrate (64 mM), at 30° C. and at pH 5.

According to the invention, it is preferred to determine the enzymatic activity in ulac units.

The amounts of laccase used in the compositions of the invention will vary as a function of the nature of the laccase chosen. Preferably, they will vary from 0.5 to 3 000 lacu, or from 1 000 to $6 \times 10^7$ u units; or from 20 to $3 \times 10^6$ ulac units, per 100 g of composition applied to the hair.

The oxidation dye precursors which may be used in the context of the present invention are chosen from those conventionally known in oxidation dyeing. Mention may be made in particular of ortho-phenylenediamines, the para-phenylenediamines of formula (I) below and the addition salts of these compounds with an acid

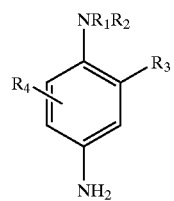

(I)

in which
$R_1$ represents a hydrogen atom or a $C_{1-4}$ alkyl, $C_{1-4}$ monohydroxyalkyl, $C_{2-4}$ polyhydroxyalkyl or 4'-aminophenyl radical,
$R_2$ represents a hydrogen atom or a $C_{1-4}$ alkyl, $C_{1-4}$ monohydroxyalkyl or $C_{2-4}$ polyhydroxyalkyl radical,
$R_3$ represents a hydrogen atom, a halogen atom such as a chlorine atom, or a $C_{1-4}$ alkyl, sulpho, carboxyl, $C_{1-4}$ monohyroxyalkyl or $C_{1-4}$ hydroxyalkoxy radical,
$R_4$ represents a hydrogen atom or a $C_{1-4}$ alkyl radical.

Among the para-phenylenediamines of formula (I) above, mention may be made in particular of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-3-methylaniline, 4-N,N-bis(β-hydroxyethyl)amino-3-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the addition salts of these compounds with an acid.

Among the para-phenylenediamines of formula (I) above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis (β-hydroxyethyl)-para-phenylenediamine and 2-chloro-para-phenylenediamine, and the addition salts of these compounds with an acid.

bis(phenyl)alkylenediamines of formula (II):

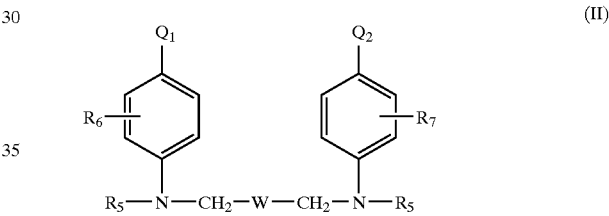

(II)

in which
$Q_1$ and $Q_2$, which may be identical or different, represent a hydroxyl radical or a radical $NHR_8$ in which $R_8$ represents a hydrogen atom or a $C_{1-4}$ alkyl radical,
$R_5$ represents a hydrogen atom or a $C_{1-4}$ alkyl, $C_{1-4}$ monohydroxyalkyl or $C_{2-4}$ polyhydroxyalkyl radical or a $C_{1-4}$ aminoalkyl radical in which the amino group may be substituted,
$R_6$ and $R_7$, which may be identical or different, represent a hydrogen or halogen atom or a $C_{1-4}$ alkyl radical,
W represents a radical chosen from the group formed by the following radicals:
—$(CH_2)_n$—; —$(CH_2)_m$—O—$(CH_2)_m$—; —$(CH_2)_m$—CHOH—$(CH_2)_m$— and —$(CH_2)_m$—N($CH_3$)—$(CH_2)_m$—;
in which n is an integer between 0 and 8 inclusive and m is an integer between 0 and 4 inclusive, and the addition salts of such compounds with an acid.

Among the bis(phenyl)alkylenediamines of formula (II) above, mention may be made in particular of N,N'-bis(β-hydroxyethyl)-N,N'-bis(4'-aminophenyl)-1,3-diamino-2-propanol, N,N'-bis(β-hydroxyethyl)-N,N'-bis(4-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl) tetramethylenediamine, N,N'-bis(β-hydroxyethyl)-N,N'-bis(4-aminophenyl) tetramethylenediamine, N,N'-bis(ethyl)-N,N'-bis(4-amino- 3-methylphenyl)ethylenediamine and the addition salts of these compounds with an acid.

Among these bis(phenyl)alkylenediamines of formula (II), N,N'-bis(β-hydroxyethyl)-N,N'-bis(4'-aminophenyl)-1,3-diamino-2-propanol, or an addition salt thereof with an acid, is recommended in particular.

the para-aminophenols corresponding to formula (III):

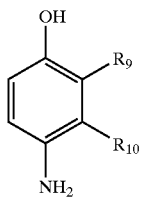

(III)

in which

R$_9$ represents a hydrogen atom or a C$_{1-4}$ alkyl, C$_{1-4}$ monohydroxyalkyl, (C$_{1-4}$-)alkoxy(C$_{1-4}$) alkyl or C$_{1-4}$ aminoalkyl, or hydroxy(C$_{1-4}$)alkoxyamino (C$_{1-4}$) alkyl radical;

R$_{10}$ represents a hydrogen or fluorine atom or a C$_{1-4}$ alkyl, C$_{1-4}$ monohydroxyalkyl, C$_{2-4}$ polyhydroxyalkyl, C$_{1-4}$ aminoalkyl, cyano(C$_{1-4}$)alkyl or (C$_{1-4}$)alkoxy (C$_{1-4}$) alkyl radical, and the addition salts of such compounds with an acid, with the proviso that at least one of the radicals R$_9$ and R$_{10}$ represents a hydrogen atom.

Among the para-aminophenols of formula (III) above, mention may be made in particular of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenyl and 4-amino-2-(β-hydroxyethylaminomethyl)phenol, and the addition salts of these compounds with an acid.

the ortho-aminophenols which may be used as oxidation bases in the context of the present invention are chosen in particular from 2-aminophenol, 2-amino-1-hydroxy-5-methylbenzene, 2-amino-1-hydroxy-6-methylbenzene and 5-acetamido-2-aminophenol, and the addition salts of these compounds with an acid;

the heterocyclic bases which may be used as oxidation bases in the context of the present invention are chosen in particular from pyridine derivatives, pyrimidine derivatives and pyrazole derivatives, and the addition salts of these compounds with an acid.

Among the pyridine derivatives, mention may be made more particularly of the compounds described, for example, in patents GB-1 026 978 and GB-1 153 196, such as 2,5-diaminopyridine, and the addition salts of such compounds with an acid.

Among the pyrimidine derivatives, mention may be made in particular of the compounds described, for example, in German patent DE-2 359 399 or Japanese patent JP-88-169 571, such as 2,4,5,6-tetraaminopyrimidine or 4-hydroxy-2,5,6-triaminopyrimidine, and the addition salts of such compounds with an acid.

Among the pyrazole derivatives, mention may be made more particularly of the compounds described in patents DE-3 843 892 and DE-4 133 957 and patent applications WO-94/08969 and WO-94/08970, such as 4,5-diamino-1-methylpyrazole, 3,4-diaminopyrazole and 4,5-diamino-1-(4'-chlorobenzyl)pyrazole, and the addition salts of these compounds with an acid.

According to the invention, the oxidation dye precursor(s) preferably represent(s) from 0.0005% to 12% by weight relative to the total weight of the composition (A) and better still from 0.005% to 6% by weight approximately.

The couplers which may be used in the dyeing process according to the invention are those conventionally used in oxidation dye compositions, i.e. meta-phenylenediamines, meta-aminophenols and meta-diphenols (resorcinols), mono- or polyhydroxylated naphthalene derivatives, sesamol and its derivatives and heterocyclic compounds such as, for example, indole couplers, indoline couplers and pyridine couplers, and the addition salts of such compounds with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethoxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts of such compounds with an acid.

When they are present, these couplers preferably represent from about 0.0001% to 10% by weight of the total weight of the composition (A) and in particular from about 0.005% to 5% by weight.

In general, the addition salts of chromogenic compounds with an acid, i.e. oxidation bases and couplers, are chosen in particular from the hydrochlorides, hydrobromides, sulphates, tartrates, lactates and acetates.

The composition (A) may contain, in addition to the oxidation dye precursors defined above and the optional combined couplers, direct dyes to enrich the shades with glints. These direct dyes may be chosen in particular from nitro dyes, azo dyes and anthraquinone dyes.

The composition (A) and/or the composition (B) may also contain at least one cationic or amphoteric substantive polymer such as those defined in EP-A-0 673 641, among which it is advantageously preferred to use:

the poly(quaternary ammonium) polymers prepared and described in French patent 2 270 846, consisting of repeating units corresponding to formula (IV) below:

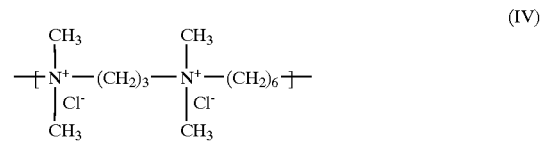

(IV)

and in which the weight-average molar mass, determined by gel permeation chromatography, is between 9 500 and 9 900;

the poly(quaternary ammonium) polymers prepared and described in French patent 2 270 846, consisting of repeating units corresponding to formula (V) below:

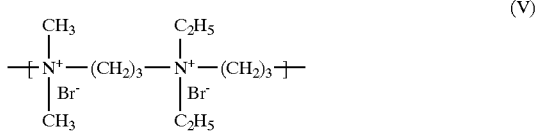

and in which the weight-average molar mass, determined by gel permeation chromatography, is about 1 200.

The medium for the composition (A) which is suitable for dyeing is preferably an aqueous medium consisting mainly of water and optionally containing cosmetically acceptable organic solvents, among which are alcohols such as ethyl alcohol, isopropyl alcohol, benzyl alcohol and phenylethyl alcohol; glycols or glycol ethers such as ethylene glycol monomethyl, monoethyl and monobutyl ethers, propylene glycol or its ethers such as propylene glycol monomethyl ether; butylene glycol; dipropylene glycol, and also diethylene glycol alkyl ethers such as, for example, diethylene glycol monomethyl or monobutyl ether, in concentrations of between about 0.5% and 20% by weight and preferably between about 2% and 10% by weight relative to the total weight of the composition.

The composition (A) may also contain an effective amount of other agents commonly used in the field of oxidation dyeing. These adjuvants are, for example, sequestering agents, hair conditioners and in particular silicones, preserving agents, opacifiers, etc., and optionally anionic, nonionic or amphoteric surfactants, or mixtures thereof.

Needless to say, a person skilled in the art will take care to select the optional additional compound(s) mentioned above, such that the advantageous properties intrinsically associated with the dye composition according to the invention are not, or are essentially not, adversely effected by the addition(s) envisaged.

The pH values for compositions (A) and (B) may be chosen in particular such that the pH value of the ready-to-use composition, resulting from mixing together the dye composition (A) and the oxidizing composition (B), is generally between 3 and 11, preferably between 4 and 9 and even more preferably between 6 and 8. They may be adjusted by means of acidifying or basifying agents that are well known in the art of oxidation dyeing of keratin fibres.

Among the basifying agents which may be mentioned, for example, are aqueous ammonia, alkali metal carbonates, alkanolamines such as monoethanolamine, diethanolamine and triethanolamine and derivatives thereof, sodium hydroxide, potassium hydroxide and compounds of formula (VI) below:

in which R is a propylene residue optionally substituted with a hydroxyl group or a $C_{1-4}$ alkyl radical; $R_{11}$, $R_{12}$, $R_{13}$ and $R_{14}$, which may be identical or different, represent a hydrogen atom or a $C_{1-4}$ alkyl or $C_{1-4}$ hydroxyalkyl radical.

The acidifying agents are conventionally, by way of example, mineral or organic acids, such as hydrochloric acid, orthophosphoric acid, carboxylic acids such as tartaric acid, citric acid or lactic acid, or sulphonic acids.

Another subject of the present invention is a ready-to-use composition for dyeing keratin fibres, which contains laccase and the oxidation dye precursor(s), or which may be obtained by mixing together the compositions (A) and (B) defined above.

The subject of the invention is also a process for dyeing keratin fibres, and in particular human keratin fibres such as the hair, using the dye compositions as defined above.

According to this process, at least one dye composition (A) as defined above with laccase or a ready-to-use dye composition as defined above is applied to the fibres for a period which is sufficient to develop the desired coloration, after which the fibres are rinsed, optionally washed with shampoo, rinsed again and dried. The time required to develop the coloration on the keratin fibres is generally between 3 and 60 minutes and more specifically between 5 and 40 minutes.

The application of the ready-to-use dye composition may take place in particular at a temperature of between room temperature (20° C.) and 60° C. and preferably between 35° C. and 50° C.

According to one particular embodiment of the invention, the process comprises a preliminary step which consists in separately storing, on the one hand, a composition (A) as defined above and, on the other hand, a composition (B) defined above, and then in mixing them together at the time of use, after which this mixture is applied to the keratin fibres.

A subject of the invention is also multi-compartment dyeing devices, or dyeing "kits" comprising at least two compartments, one of which contains a composition (A) containing at least one oxidation dye precursor and optionally one or more couplers and, as reducing agent, N-acetylcysteine, and another contains an oxidizing composition (B) containing at least one laccase. These devices may be equipped with a means for applying the desired mixture to the hair, such as the devices described in patent FR-2 586 913.

Needless to say, the preceding description has been given purely by way of illustration and with no limitation, and that variants or modifications may be made thereto in the context of the present invention.

Concrete examples illustrating the invention will now be given, without, however, being limiting in nature.

COMPARATIVE EXAMPLES

The dye compositions below are prepared (contents in grams):

| EXAMPLE | 1 (*) | 2 (*) | 3 | 4 (*) |
|---|---|---|---|---|
| para-Phenylenediamine ($10^{-3}$ mol) | 0.108 g | 0.108 g | 0.108 g | 0.108 g |
| 1-Methyl-2-hydroxy-4-aminobenzene ($10^{-3}$ mol) | 0.123 g | 0.123 g | 0.123 g | 0.123 g |
| N-Acetyl-L-cysteine | — | — | 0.1 g | — |
| Glucose | — | 5 g | — | — |
| Erythorbic acid | — | — | — | 0.3 g |
| Phosphate buffer sold under the name Titrisol by the company Merck | pH 7 | pH 7 | pH 7 | pH 7 |
| Demineralized water qs | (100-x) g | (100-x) g | (100-x) g | (100-x) g |

(*) Examples not in accordance with the invention

At the time of use, x g of a laccase solution is added in order to obtain a final dye composition with a laccase concentration equal to $10^7$ u units. Next, each of the dye compositions obtained was applied to locks of natural grey hair containing 90% white hairs, at a rate of 5 g of composition per g of hair, for 30 minutes at 40° C. The hair was then rinsed, washed with shampoo, washed again and then dried.

The hair dyed with compositions 1*, 2* and 3 had the same shade (mid red-purple).

In order to determine the rise of the coloration more precisely, the colour of the locks was evaluated before and after dyeing in the Munsell system, using a Minolta CM-2002® calorimeter.

According to the Munsell notation, a colour is defined by the expression H V/C in which the three parameters denote, respectively, the shade or Hue (H), the intensity or Value (V) and the purity or Chromaticity (C), the oblique line in this expression simply being a convention and not representing a ratio.

The difference between the colour of the lock before dyeing and the colour of the lock after dyeing expresses the intensity of the coloration and was calculated by applying the Nickerson formula:

$$\Delta E = 0.4\ C_0 \Delta H + 6 \Delta V + 3 \Delta C$$

as described, for example, in "Couleur, Industrie et Technique"; pages 14–17; vol. No. 5; 1978.

In this formula, $\Delta E$ represents the difference in colour between two locks, $\Delta H$, $\Delta V$ and $\Delta C$ represent the variation in absolute value of the parameters H, V and C, and $C_0$ represents the purity of the lock relative to which it is desired to evaluate the colour difference.

The greater the value of $\Delta E$, the more intense the coloration.

The results are given in the table below.

| Composition | $\Delta E$ |
|---|---|
| 1 (*) | 30.94 |
| 2 (*) | 31.29 |
| 3 | 32.07 |
| 4 (*) | 5.75 |

These results show that composition 2 not in accordance with the invention and composition 3 in accordance with the invention give a coloration which is as intense as composition 1 not in accordance with the invention and which contains no reducing agent. On the other hand, the coloration obtained with composition 4* using erythorbic acid as reducing agent is weak. Thus, the use of N-acetylcysteine does not impede the rise of the coloration, and makes it possible to obtain colorations that are as intense as those obtained without reducing agent.

The dye compositions 2* and 3 mentioned above were also stored at an ambient temperature of 22° C.±2° C. for 2 weeks.

The same colorations as those described above were then carried out.

The results are given in the table below:

| Composition | $\Delta E$ |
|---|---|
| 2 (*) | 13.58 |
| 3 | 31.35 |

Thus, only the use of N-acetylcysteine as reducing agent makes it possible to reduce the oxidation of the dye precursors while at the same time not modifying over time the rise in coloration on the fibres.

What is claimed is:

1. A composition for dyeing keratin fibers, stored protected from air, containing, in a medium which is suitable for dyeing, at least one oxidation dye precursor and, as a reducing agent, from 0.01% to 0.25% by weight of N-acetylcysteine, and at least one laccase.

2. A composition comprising a mixture of a composition (A) including at least one oxidation dye precursor and from 0.01% to 0.25% by weight N-acetylcysteine in a medium suitable for dyeing a keratin fiber and a composition (B) including at least one laccase in an alkaline, neutral or acidic medium, wherein said composition is ready-to-use to dye a keratin fiber.

3. A process for dyeing keratin fibers which comprises:
    applying to the fibers a dye composition (A) comprising at least one oxidation dye precursor and from 0.01% to 0.25% by weight of N-acetylcysteine as a reducing agent in a medium which is suitable for dyeing; and
    developing the color in the presence of air in an alkaline, neutral or acidic medium using a composition (B) comprising at least one laccase, the compositions (A) and (B) being mixed together immediately before use or applied one after the other to the keratin fibers.

4. The process according to claim 3, wherein the laccase is selected from the group consisting of plant laccases, animal laccases, fungal laccases, bacterial laccases, and recombinant laccases.

5. The process according to claim 3, wherein the laccase is produced by plants which carry out chlorophyll synthesis.

6. The process according to claim 5, wherein the laccase is extracted from an *Anacardiacea* plant; from a *Podocarpacea* plant; from *Rosmarinus* off.; from *Solanum tuberosum*; from *Iris* sp.; from *Coffea* sp.; from *Daucus carrota*; from *Vinca minor*; from *Persea americana*; from *Catharenthus roseus*; from *Musa* sp.; from *Malus pumila*; from *Gingko biloba*; from *Monotropa hypopithys* (Indian pipe); from *Aesculus* sp.; from *Acer pseudoplatanus*; from *Prunus persica*; and from *Pistacia palaestina*.

7. The process according to claim 4 wherein the laccase is obtained from *Pyricularia orizae, Polyporus versicolor, Rhizoctonia praticola, Rhus vernicifera, Scytalidium, Polyporus pinsitus, Myceliophthora thermophila, Rhizoctonia solani, Trametes versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserine, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Paneolus papilionaceus, Panaeolus sphinctrinus, Schizophyllum commune, Dichomitius squalens*, or variants thereof.

8. The process according to claim 3, wherein the laccase is present in amounts ranging from 0.5 to 3,000 lacu per 100 g of the composition applied to the keratin fibres.

9. The process according to claim 3, wherein the oxidation dye precursors of the composition (A) are selected from the group consisting of: ortho- and para-phenylenediamines; bis(phenyl)alkylenediamines; ortho- and para-aminophenols; heterocyclic bases; and addition salts thereof with an acid.

10. The process according to claim 9, wherein the oxidation dye precursors are present in a proportion of 0.0005% to 12% by weight relative to the total weight of the composition (A).

11. The process according to claim 9, wherein the addition salts are selected from the group consisting of hydrochlorides, hydrobromides, sulphates, tartrates, lactates, and acetates.

12. The process according to claim 3, wherein the composition (A), the composition (B), or a mixture thereof further comprises direct dyes.

13. The process according to claim 3, wherein the composition (A), the composition (B), or a mixture thereof further comprises at least one cationic or amphoteric substantive polymer.

14. The process according to claim 13, wherein the substantive polymer is a poly(quaternary ammonium) polymer consisting of repeating units corresponding to formula (IV) below:

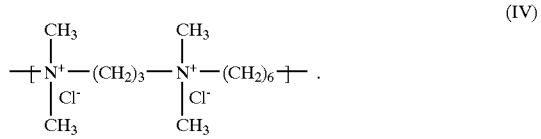

15. The process according to claim 13, wherein the substantive polymer is a poly(quaternary ammonium) polymer consisting of repeating units corresponding to formula (V) below:

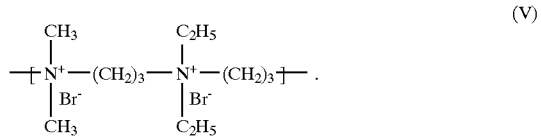

16. The process according to claim 3, wherein the composition (A) further comprises one or more adjuvants selected from the group consisting of sequestering agents, hair conditioners, silicones, preserving agents, opacifiers, anionic, nonionic or amphoteric surfactants, and mixtures thereof.

17. The process according to claim 3, wherein the pH value of the composition applied to the keratin fibers is between 3 and 11.

18. A process for dyeing keratin fibers according to claim 1 which comprises applying to the keratin fibers at least one composition according to claim 1 containing at least one laccase, for a period which is sufficient to develop the desired coloration.

19. The process according to claim 18, wherein the composition is applied at a temperature of between 20° C. and 60° C.

20. The process according to claim 3, wherein the keratin fibers are human.

21. The process according to claim 3, wherein the laccase is present in amounts ranging from 1,000 to $6 \times 10^7$ u units per 100 g of the composition applied to the keratin fibers.

22. The process according to claim 3, wherein the laccase is present in amounts ranging from 20 to $3 \times 10^6$ ulac units per 100 g of the composition applied to the keratin fibers.

23. The process according to claim 3, wherein the pH value of the composition applied to the keratin fibers is between 4 and 9.

24. The process according to claim 3, wherein the pH value of the composition applied to the keratin fibers is between 6 and 8.

25. A process for dyeing keratin fibers which comprises applying to the keratin fibers at least one composition according to claim 2 for a period which is sufficient to develop the desired coloration.

26. The process according to claim 2, wherein the composition is applied at a temperature of between 35° C. and 50° C.

27. A kit for dyeing keratin fibers comprising the composition according to claim 1 after the number 21.

28. The process according to claim 9, wherein the addition salts are selected from the group consisting of hydrochlorides, hydrobromides, sulphates, tartrates, lactates, and acetates.

29. The process according to claim 16, wherein the hair conditioner is a silicone.

30. The process according to claim 3, wherein composition (A) further includes one or more couplers.

31. The process according to claim 30, wherein the couplers of the composition (A) are selected from the group consisting of meta-phenylenediamines, meta-aminophenols, meta-diphenols and heterocyclic couplers, and the addition salts thereof with an acid.

32. The process according to claim 30, wherein the couplers are present in a proportion of 0.0001% to 10% by weight relative to the total weight of the composition (A).

33. A multi-compartment device, for dyeing keratin fibers comprising one compartment containing a composition (A) including at least one oxidation dye precursor and from 0.01% to 0.25% by weight of N-acetylcysteine, and a second compartment containing an oxidizing composition (B) including at least one laccase.

* * * * *